United States Patent [19]

Peterson et al.

[11] 3,988,144

[45] Oct. 26, 1976

[54] NOVEL ORGANOTIN COMPOUNDS

[75] Inventors: Donald J. Peterson, Springfield Township, Hamilton County; James F. Ward, Fairfield Township, Butler County; Ralph A. Damico, Colerain Township, Hamilton County, all of Ohio

[73] Assignee: The Procter & Gamble Company, Cincinnati, Ohio

[22] Filed: Mar. 19, 1975

[21] Appl. No.: 560,006

Related U.S. Application Data

[62] Division of Ser. No. 410,057, Oct. 26, 1973, Pat. No. 3,897,553, which is a division of Ser. No. 184,225, Sept. 27, 1971, Pat. No. 3,808,264.

[52] U.S. Cl. .................................. 71/91; 71/97; 424/275; 424/288
[51] Int. Cl.² ................................................ A01N 9/14
[58] Field of Search ................................ 71/91, 97

[56] References Cited
UNITED STATES PATENTS

| | | | |
|---|---|---|---|
| 2,898,205 | 8/1959 | Pyne et al. | 71/91 |
| 2,928,766 | 3/1960 | Rosen | 71/91 |
| 2,975,194 | 3/1961 | Berkey | 71/91 |
| 2,976,297 | 3/1961 | Bluestone | 71/91 |
| 3,497,537 | 2/1970 | Fish | 71/97 |
| 3,723,089 | 3/1973 | Peterson | 71/97 |
| 3,725,446 | 4/1973 | Peterson | 71/97 |
| 3,897,560 | 7/1975 | Peterson | 71/97 |

*Primary Examiner*—Glennon H. Hollrah
*Attorney, Agent, or Firm*—Rose Ann Dabek; Jerry J. Yetter; Richard C. Witte

[57] ABSTRACT

Novel organotin-substituted cyclic sulfone compounds of the general formula:

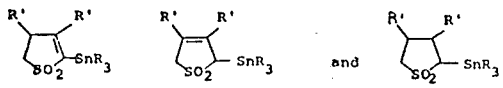

where each R is alkyl of from 1 to about 14 carbon atoms, or aryl and each R' is alkyl of from 1 to about 14 carbon atoms, aryl or hydrogen, and a process for preparing same. These organotin compounds have insecticidal, acaricidal, bacteriostatic, fungicidal and herbicidal properties.

2 Claims, No Drawings

NOVEL ORGANOTIN COMPOUNDS

This is a division of application Ser. No. 410,057, filed Oct. 26, 1973, now U.S. Pat. No. 3,897,553 which is a division of application Ser. No. 184,225, filed Sept. 27, 1971, now U.S. Pat. No. 3,808,264.

BACKGROUND OF THE INVENTION

This invention relates to novel organotin compounds, a method for their preparation, pesticidal and herbicidal compositions containing said compounds, and to a method of combating pests and unwanted vegetation.

The desirability of controlling or eradicating insect pests and common disease-causing organisms is clearly accepted. Thus, compounds possessing insecticidal, acaricidal, bacteriostatic and fungicidal properties especially adapted to such control or eradication are or particular importance.

The necessity of controlling or eradicating unwanted plants, e.g., weeds from fields planted with growing crops, by means of chemical herbicides is also clearly accepted. Such chemical control of undesirable plant growth is more efficient and less expensive than manual control. However, the chemical control of weeds in the presence of growing food crops has been somewhat hindered because of several factors. For example, many herbicides are unsuitable for use with food crops because of toxic residues remaining on the crops after application.

Certain organotin compounds have been previously disclosed for use as pesticides, herbicides, and the like; see the co-pending application of Peterson, entitled "Novel Organotin Compounds", Ser. No. 164,941, filed July 21, 1971 now U.S. Pat. No. 3,784,580. The preparation of certain organotin-sulfur compounds is described in the co-pending application of Peterson, entitled "Preparation of Organotin Compounds", Ser. No. 158,528, filed June 30, 1971 now U.S. Pat. No. 3,794,670.

Many useful organotin compounds are relatively expensive and it is an object of this invention to provide novel, relatively inexpensive organotin compounds and a method for their preparation. A further object is to provide novel organotin-substituted sulfolene and sulfolane compounds which are useful as insecticides, acaricides, bacteriostats, fungicides and herbicides. Another object is to provide pesticidal compositions containing the novel organotin-substituted sulfolene and sulfolane compounds. A still further object is to provide novel compositions and methods effective for combating insects and other pests, such as weeds, and bacterial and fungal organisms. These and other objects are obtained by this invention as will be apparent from the following disclosure.

SUMMARY OF THE INVENTION

The novel organotin-substituted sulfolene and sulfolane compoounds of the present invention are of the formula:

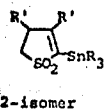 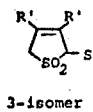 and 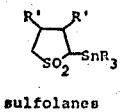

2-isomer    3-isomer    sulfolanes where each R is selected from the group consisting of alkyl of from 1 to about 14 carbon atoms (e.g., methyl, ethyl, n-propyl, iso-propyl, n-butyl, iso-butyl, amyl, iso-amyl, hexyl, n-octyl, n-dodecyl, n-tetradecyl); aryl (e.g., phenyl, naphthyl); substituted aryl (e.g., p-methoxyphenyl, p-tolyl, p-chlorophenyl, o-methoxyphenyl); and each R' is alkyl of from 1 to about 14 carbon atoms, aryl, or hydrogen.

In its process aspect, this invention comprises reacting an organotin amine compound of the formula: $(R_3Sn)_xNR''_{3-x}$, wherein $x$ is an integer from 1 to 3, R is as disclosed above, and each R'' is selected from the group consisting of alkyl ($C_1$ to $C_{10}$) or hydrogen, with a sulfolene or sulfolane compound of the formula:

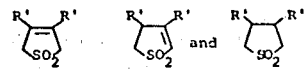

wherein R' is as disclosed above, to yield the isomeric organotin-2-sulfolenes, organotin-3-sulfolenes and organotin-substituted sulfolanes of the type disclosed above, respectively.

The present invention also encompasses pesticidal compositions (a term which includes insecticides, herbicides, acaricides and the like) comprising one or more of the organotin-substituted sulfolene or sulfolane compounds disclosed herein and a carrier vehicle of the type hereinafter disclosed.

DETAILED DESCRIPTION OF THE INVENTION

The isomeric organotin-2-sulfolene and organotin-3-sulfolene compounds of this invention can be prepared by various methods. For example, 2-sulfolenes can be metalated by any of the common metalating agents (e.g., n-butyllithium) to provide the corresponding metalated sulfolene which can be subsequently reacted with a triorganotin halide. However, such processes require the use of extremely low reaction temperatures and expensive reagents and equipment.

In accordance with the process aspects of the present invention, the isomeric organotin sulfolene compounds of this invention are prepared by reacting 3-sulfolene compounds with an organotin amine compound according to the following gross scheme:

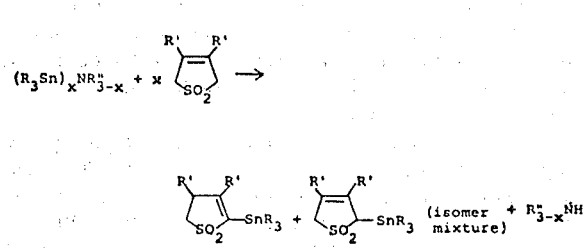

wherein R, R' and R'' are as hereinabove defined. Trialkyltin amines ($C_1$–$C_{20}$) are preferred in this process; the tributyltin amines are especially preferred. The 2-sulfolene isomers can also be used in this process, but are not preferred in that they must first be prepared by base isomerization of the 3-sulfolene compound, thereby requiring an additional step. The organotin-substituted sulfolane compounds herein are prepared in like manner using an organotin amine and a sulfolane compound of the type disclosed above.

The organotin amine compounds used in the present process can be prepared by reacting the alkali metal salts of ammonia and primary and secondary amines with triorganotin halides, e.g., triorganotin fluorides, chlorides, bromides and iodides, which are commercially available. The alkali metal salts of primary and secondary amines and ammonia are themselves prepared by reacting said amines with the corresponding metals in the manner well-known to those skilled in the art. For example, ammonia will react with sodium to yield sodamide which, in turn, will react with a triorganotin halide to prepare the corresponding organotin amine. Dimethylamine will react with lithium metal in the presence of a conjugated diene such as butadiene to form lithium dimethylamide, which, in turn, reacts with a triorganotin halide to form the N,N-dimethylaminoorganotin compound. Alternatively, various amines can be metalated in standard fashion with, for example, organolithium compounds to provide the metal amine salts. In general terms, the preparation of the organotin amines useful in the preparation of the organotin sulfolene and sulfolane compounds of this invention is represented by the following reaction sequence:

$$R''_2NH + C_4H_9M \rightarrow R''_2NM + C_4H_{10} \quad \text{or,}$$

$$2R''_2NH + 2M \rightarrow 2R''_2NM + H_2 \quad \text{then,}$$

$$R''_2NM + R_3SnX \rightarrow R''_2NSnR_3 + MX.$$

wherein M is alkali metal, i.e., lithium, sodium, potassium, rubidium, and cesium; wherein R and R'' are as defined above; and wherein X is a halogen, i.e., fluoride, chloride, bromide and iodide. It will be recognized that when primary amines, secondary amines and ammonia are used herein, organotin amines of the formula $R_3SnNR''_2$, $(R_3Sn)_2NR''$ and $(R_3Sn)_3N$ are formed. These are all useful in the present process. Sodium is a preferred alkali metal for use in preparing the alkali meta salts of the amine. Any nitrogenous compound having an N—H bond capable of reacting with a metalating agent to form an alkali metal amine salt is suitable for preparing the organotin amines used herein. Exemplary amines used in this procedure include methylamine, dimethylamine, ethylamine, diethylamine, decylamine, di-decylamine, cyclohexylamine, di-cyclohexylamine, ethylene diamine, and isopropylamine, as well as ammonia. Especially preferred herein are ammonia, methylamine, dimethylamine and diethylamine, for economic reasons.

The triorganotin halides suitable for preparing the organotin amines used herein are commercially available. Such compounds are prepared, for example, by reacting an organometallic compound with a tin tetrahalide in the manner well-known to those skilled in the art. Exemplary triorganotin halides suitable for preparing the organotin amines used in the present process include trimethyltin chloride, triethyltin bromide, tripropyltin fluoride, tributyltin chloride, triphenyltin iodide, trinaphthyltin chloride, tri-p-tolyltin chloride, tri-m-methoxyphenyltin iodide, tris-eicosyltin chloride and the like. The trialkyltin chlorides are preferred for economic reasons. Tributyltin chloride is most preferred herein.

From the foregoing it may be seen that a variety of organotin amines useful in the present process can be readily prepared using standard techniques. Preferred organotin amines used in the present process are the trialkyltin amines, especially the bis(trialkyltin)amines [$(R_3Sn)_2NH$], tris-(trialkyltin)amines [$(R_3Sn)_3N$], bis-(trialkyltin)-N-methylamines [$(R_3Sn)_2NCH_3$], aminotrialkyltins ($R_3SnNH_2$), and N,N-di-methylaminotrialkyltins [$R_3SnN(CH_3)_2$]. Of these, the compounds wherein R is butyl, e.g., aminotributyltin, (N-methylamino)tributyltin, (N,N-dimethylamino)tributyltin, bis-(tributyltin)amine, tris-(tributyltin)amine and bis-(tributyltin)-N-methylamine, are preferred. When ease of preparation and handling are of primary concern, (N,N-diethylamino)tributyltin or (N,N-dimethylamino)tributyltin are preferably used. For economy, tris-(tributyltin)amine is preferred.

The sulfolene compounds used in the reaction with the organotin amines to prepare the organotin-substituted sulfolenes can be either the isomeric 3-sulfolene or 2-sulfolene compounds, or mixtures thereof. The 3-isomers are preferred herein in that they are prepared directly from $SO_2$ and dienes of the formula $CH_2$=$CR'$—$CR'$=$CH_2$ (R' as above) in well-known fashion. For example, 1,3-butadiene, 2,3-dimethylbutadiene, 2-ethylbutadiene, 2,3-diphenylbutadiene, 2-tetradecylbutadiene, 2-naphthylbutadiene, 2-p-tolylbutadiene, 2-p-chlorophenylbutadiene, 2-o-methoxyphenylbutadiene, 2-isopropylbutadiene and isoprene are reacted with $SO_2$ to yield 3-sulfolene, 3,4-dimethyl-3-sulfolene, 3-ethyl-3-sulfolene, 3,4-diphenyl-3-sulfolene, 3-tetradecyl-3-sulfolene, 3-naphthyl-3-sulfolene, 3-p-tolyl-3-sulfolene, 3-p-chlorophenyl-3-sulfolene, 3-o-methoxyphenyl-3-sulfolene, 3-isopropyl-3-sulfolene and 3-methyl-3-sulfolene, respectively, all of which are suitable for use in the preparation of the organotin-substituted sulfolene compounds of this invention by means of the organotin amine reaction described above. Preferred herein for economic reasons are 3-sulfolene and 3-methyl-3-sulfolene.

Alternatively, the 3-sulfolene compounds are first isomerized to the 2-sulfolene isomers by treatment with base (e.g., NaOH, KOH, etc.) and can be used in the metalation procedure disclosed above to prepare the organotin-substituted 2-sulfolene compounds of this invention. In this general fashion, butadiene is reacted with $SO_2$ to yield 3-sulfolene; subsequent contact with aqueous NaOH yields 2-sulfolene useful in the synthesis of the organotin-substituted 2-sulfolenes by the metalation procedure. Similarly, reaction of $SO_2$ with isoprene followed by base treatment yields 3-methyl-2-sulfolene. In like manner, 2-phenyl-1,3-butadiene, 2-naphthyl-1,3-butadiene, 2-dodecyl-1,3-butadiene, 2,3-dimethylbutadiene, and 2-p-tolyl-1,3-butadiene are reacted with $SO_2$ and isomerized with base to yield 3-phenyl-2-sulfolene, 3-naphthyl-2-sulfolene, 3-dodecyl-2-sulfolene, 3,4-dimethyl-2-sulfolene and 3-p-tolyl-2-sulfolene, respectively, which are all useful in preparing the organotin-substituted 2-sulfolene compounds of this invention. Preferably, the 2-sulfolene compounds can be used with the organotin amines in the manner hereinabove detailed to prepare the compounds of this invention.

The sulfolane compounds used in conjunction with the organotin amines in the manner of this invention to prepare organotin-substituted sulfolanes are obtained by hydrogenation of any of the 2- and 3-sulfolenes disclosed above using well-known procedures. For example, hydrogenation of 3-sulfolene using a palladium-on-carbon catalyst yields sulfolane, which is suitable for use herein. Raney nickel hydrogenation of 3-methyl-3-sulfolene yields 3-methylsulfolane, which is also useful herein.

The preferred process of this invention is carried out by admixing the organotin amine with the 3-sulfolene isomer or sulfolane compound in accordance with the stoichiometry noted in the reaction schemem listed above (mole ratios of from about 1:100 to 100:1, preferably about 1:1 are suitable). The reaction mixture is heated at a temperature above about 40° C for a period from about 1 to about 72 hours, and the organotin-substituted sulfolene or sulfolane compound is recovered by crystallization, chromatography or distillation, depending on the physical form of the compound being prepared. For example, liquid organotin 2-sulfolene and sulfolane compounds are generally recovered by distillation while the solid organotin sulfolene and sulfolane and liquid 3-sulfolene compounds are readily recovered by column chromatography or crystallization. When sulfolenes are being prepared by this method, both the organotin-3-sulfolene and the organotin-2-sulfolene isomers are formed during the reaction due to isomerization. The isomer mixture can be separated into its components, e.g., chromatographically, if so desired and both isomers are useful as pesticides, and the like. Alternatively, and preferably from an economic standpoint, the isomers are not separated but are employed as mixtures as pesticides in the manner hereinafter described. Of course, the sulfolanes do not form double bond isomers.

While the process for preparing organotin-substituted sulfolenes and sulfolanes using organotin amines can be carried out without a solvent, it is sometimes convenient to use a solvent or suspending liquid herein. Any of the common organic solvents can be used for this purpose, including for example, hexane, benzene, toluene, xylene, and the like. Mixtures such as the petroleum ethers and the glyme solvents are also suitable. Preferred herein are anhydrous aprotic organic liquids, especially hexane. Sufficient liquid is used to dissolve or disperse the reactants.

The reaction temperature in the present process is not critical except that the temperature should be above about 40° C, more preferably from about 50° to about 150° C, to insure that the reaction will occur at a reasonable rate. Likewise, the reaction is initiated almost immediately and the reaction time employed will vary with temperature, the amount of organotin amine being reacted with the sulfolene or sulfolane compound, and the like. Usually, from about 10 minutes to 24 hours per mole of organotin-substituted sulfolene or sulfolane compound being prepared is sufficient.

The organotin-substituted sulfolene and sulfolane compounds, singly, as mixtures, and as isomer mixtures, are useful as insecticides, acaricides, bactericides, bacteriostats, fungicides, fungistats, and herbicides. The present invention also encompasses a process for combating pests comprising applying the organotin-substituted sulfolene and sulfolane compounds herein to loci infested with pests, i.e., insects, larvae, bacteria, fungi, or undesirable vegetation, either singly, in combination with one another or with other well-known pesticides, herbicides, and biocides, to provide the desired effects. Application rates are approximately those of other well-known herbicides, insecticides, and the like. For example, use of about 10 p.p.m. of the organotin-substituted sulfolene compounds in bacterial culture media kills substantially all the bacteria therein. Application of the organotin-substituted sulfolene compounds to undesired vegetation at a rate of from about 0.5 to about 50 pounds, more preferably about 1 pound to about 3 pounds, per acre results in herbicidal effects.

For practical use as herbicides, insecticides and the like, the organotin-substituted sulfolene and sulfolane compounds herein are incorporated into compositions comprising a carrier and an effective, i.e., herbicidal, bacteriostatic, fungicidal, or insecticidal, amount of one or more of the organotin-substituted sulfolene or sulfolane compounds. (As used herein, the term "carrier" is defined as an inert solvent or dry bulking agent of the type hereinafter disclosed which has no substantial insecticidal, herbicidal, etc., effectiveness, but which provides a means whereby the organotin-substituted sulfolene and sulfolane compounds can be diluted for convenient application.) Such compositions can then be applied conveniently in any desired quantity. These compositions can be solids, such as dust, granules, or wettable powders, or they can be liquids such as solutions, aerosols, or emulsifiable concentrates. The solid compositions generally contain from about 1 to about 95% by weight of the organotin-substituted sulfolene or sulfolane compounds and the liquid compositions generally contain from about 0.5 to about 70% by weight of said compounds.

The organotin-substituted sulfolene and sulfolane compounds herein are conveniently applied as solutions, emulsifiable concentrates, wettable powders, dusts, aerosols and the like. Suspensions or dispersions of the compounds of this invention in a non-solvent, such as water, are suitable, as are solutions of the insecticides, acaricides, herbicides, and fungicides of this invention in oil which is emulsified in water. Examples of oil solvents include hydrocarbons such as benzene and toluene, kerosene, Stoddard solvent, and halogenated hydrocarbons such as chlorobenzene, chloroform, fluorotrichloromethane and dichlorodifluoromethane.

Emulsifiers and wetting agents are also useful in the compositions herein. Such materials are surface active agents of the anionic, nonionic (preferred), cationic, ampholytic and zwitterionic type and normally comprise from about 0.1 to 5% by weight of the compositions herein. Examples of suitable anionic surface active agents are sodium salts of fatty alcohol sulfates having from 8–18 carbon atoms in the fatty chain and sodium salts of alkyl benzene sulfonates having from 9 to 15 carbon atoms in the alkyl chain. Examples of suitable nonionic surface active agents are the polyethylene oxide condensates of alkyl phenols, wherein the alkyl chain contains from about 6 to 12 carbon atoms and the amount of ethylene oxide condensed onto each mole of alkyl phenol is from about 5 to 25 moles. An especially preferred nonionic herein is the polyethylene oxide condensate of sorbitan mono-oleate (Tween). Examples of suitable cationic surface active agents are dimethyl dialkyl quaternary ammonium salts wherein the alkyl chains contain from about 8 to 18 carbon atoms and the salt forming anion is a halogen. Examples of suitable ampholytic surface active agents are derivatives of aliphatic secondary or tertiary amines in which one of the aliphatic substituents contains from about 8 to 18 carbon atoms and one contains an anionic water solubilizing groups, e.g., sulfate or sulfonate. Specific suitable ampholytic surface active agents are sodium-3-dodecylaminopropionate and sodium-3-dodecyl amino propane sulfonate. Examples of suitable zwitterionic surface active agents are derivatives of aliphatic quaternary ammonium compounds in which one of the aliphatic constituents contains from about 8 to 18 carbon atoms and one contains an anionic water solubilizing group. Specific examples of zwitterionic surface active agents are 3-(N,N-dimethyl-N-hexadecylammonio)propane-1-sulfonate and 3-(N,N-dimethyl-N-hexadecylammonio)-2-hydroxy propane-1-sulfonate. Many other suitable surface active agents are described in "Detergents and Emulsifiers — 1969 Annual", by John W. McCutcheon, Inc., which is incorporated by reference herein. Suitable solvents for emulsifiable concentrates comprising the organotin-substituted sulfolene or sulfolane compounds and an emulsifier include hydrocarbons such as benzene, toluene, xylene, kerosene and Stoddard Solvent and halogenated hydrocarbons such as chlorobenzene, chloroform, and the like.

Aerosols prepared by dissolving the compounds of this invention in a highly volatile liquid carrier such as trifluorochloromethane, nitromethane, and the like, or by dissolving such compounds in a less volaile solvent, such as benzene, and admixing the resulting solution with a highly volatile liquid aerosol carrier, can also be employed to advantage.

Compositions in the form of dusts can be prepared by admixing the compounds of this invention with dry free-flowing powders such as clay, bentonite, fuller's earth, diatomaceous earth, pyrophyllite, attapulgite, calcium carbonate, chalk and the like. Wettable dusts also include from about 0.1 to 5% by weight of one or more of the surface active agents described above.

Preferred compositions herein suitable for use as pesticides, i.e., insecticides, acaricides, herbicides, bactericides and fungicides, comprise from about 1 to about 10% by weight of one or more of the organotin-substituted sulfolene or sulfolane compounds disclosed herein (the sulfolenes are preferred for economic reasons), from about 0.1 to about 5% by weight of a surface active agent of the type hereinabove disclosed, and from about 85 to about 99% by weight of a carrier. Preferred organotin-substituted sulfolene compounds in such compositions are 2-tributyltin-3-methyl-2-sulfolene, 2-tributyltin-3-methyl-3-sulfolene, 2-tributyltin-2-sulfolene, 2-tributyltin-3-sulfolene, and mixtures thereof; preferred sulfolanes are 2-tributyltinsulfolane and 2-tributyltin-3-methylsulfolane. Preferred surface active agents in such compositions are the nonionics, especially the polyethylene oxide condensates of sorbitan monooleate. Preferred carriers in such compositions include acetone, water, kerosene, Stoddard solvent, and mixtures thereof.

The following examples are intended to illustrate the compounds, compositions and processes of this invention but are not intended to be limiting thereof. The sulfolene compounds used in the processes are available commercially or can be prepared by reacting sulfur dioxide with a diene in the manner well-known in the art.

EXAMPLE I

Preparation of 2-Tributyltin-3-methyl-2-sulfolene 5.0 g. of 3-methyl-2-sulfolene was dissolved in 220 ml. of tetrahydrofuran (THF) at −65° C. 2.56 g. of 1.6 molar n-butyllithium was added to the sulfolene-THF solution over 20 minutes; the solution was stirred at −65° C for about 45 minutes. 13.5 g. of tributyltin chloride (10% excess) was added dropwise to the above solution at −65° C. The reaction mixture was stirred for about 1 hour and the solvent evaporated. The liquid residue was dissolved in chloroform and solid LiCl removed by filtration. The liquid recovered by the evaporation of the chloroform was analyzed and corresponded to 2-tributyltin-3-methyl-2-sulfolene.

In the above procedure, the tributyltin chloride is replaced by an equivalent amount of triphenyltin bromide, tri-p-toyltin iodide, tri-o-methoxyphenyltin chloride, trinaphthyltin chloride and tri-hexadecyltin bromide, respectively, and the compounds 2-triphenyltin-3-methyl-2-sulfolene, 2-tri-p-tolyltin-3-methyl-2-sulfolene, 2-tri-o-methoxyphenyltin-3-methyl-2-sulfolene, 2-tri-naphthyltin-3-methyl-2-sulfolene and 2-trihexadecyltin-3-methyl-2-sulfolene, respectively, are secured.

In the above procedure, the 3-methyl-2-sulfolene is replaced by an equivalent amount of 2-sulfolene, 3-octyl-2-sulfolene, and 3-phenyl-2-sulfolene, respectively, and the compounds 2-tributyltin-2-sulfolene, 2-tributyltin-3-octyl-2-sulfolene, and 2-tributyltin-3-phenyl-2-sulfolene, respectively, are secured.

EXAMPLE II

Reaction of 3Methyl-3-sulfolene with (N,N-dimethylamino)tributyltin

To a mixture comprising 9 g. of dimethylamine in 100 ml. of dry hexane at 0° C was added 100 ml. of 1.6 molar butyllithium in n-hexane at a rate such that the temperature remained less than about 10° C. The solution was stirred for 1 hour at ambient temperature. Tributyltin chloride (52.6 g.) was added dropwise to the stirred reaction mixture at 10° C and the reaction mixture was allowed to warm to room temperature with stirring for about 1 hour. The lithium chloride whch had formed was filtered and the hexane removed by evaporation to yield (N,N-dimethylamino)tributyltin.

10.0 g. of (N,N-dimethylamino)tributyltin, prepared above, and 4.0 g. of 3-methyl-3-sulfolene (commercial material) were mixed in a 25 ml. flask and stirred at 75° C for 4 hours. An NMR spectrum of the reaction material indicated that no N—$CH_3$ groups remained in the reaction mixture, indicating a loss of dimethylamine. The reaction mixture was chromatographed on 150 g. of silica gel and yielded a material which proved to be a mixture of 2-tributyltin-3-methyl-2-sulfolene and 2-tributyltin-3-methyl-3-sulfolene.

In the above procedure the (N,N-dimethylamino)-tributyltin is replaced by an equivalent amount of (N,N-dimethylamino)triphenyltin, (N,N-dimethylamino)-tri-p-tolyltin, (N,N-diethylamino)tri-m-chlorophenyltin, (N-methylamino)tri-o-fluorophenyltin, tris-(tri-m-nitrophenyltin)amine and aminotri-tetradecyltin, respectively, and mixtures of the corresponding organotin-substituted 2- and 3-sulfolene isomers are secured.

EXAMPLE III

Reaction of 3-sulfolene with tris-(trialkyltin)amines

A 500 ml. flask is fitted with a cold finger condenser cooled with a dry-ice acetone mixture and blanketed with argon gas. Anhydrous ammonia gas is condensed into the reaction flask (ca. 300 ml. liquified gas). 0.08 g. of iron (III) chloride and 2.57 g. of sodium metal are added to the flask portion-wise over 30 minutes. After hydrogen evolution ceases, tributyltin chloride (ca. 0.1 mole) is added dropwise to the reaction mixture; a black oily material [mixture of mono-, bis- and tris- (tributyltin)amine] is formed. 250 ml. of diethyl ether is added to the reaction vessel to disperse the oily material and 0.10 of 3-sulfolene is added thereto. The reaction mixture is stirred for about 30 minutes, and the ammonia and ether allowed to evaporate, leaving a black residue. The residue is heated at about 100° C for approximately 5 hours, washed with 100 ml. of aqueous 1M $NH_4Cl$ and extracted with 3 × 200 ml. portions of diethyl ether. The product is chromatographed on silica gel and provides a mixture of 2-tributyltin-3-sulfolene and 2-tributyltin-2-sulfolene.

In the above procedure, the 3-sulfolene is replaced by an equivalent amount of 2-sulfolene, 3,4-dimethyl-3-sulfolene, 3-ethyl-4-phenyl-3-sulfolene, 3-naphthyl-4-decyl-3-sulfolene, and 3,4-dioctyl-2-sulfolene, respectively, and the following are secured: 2-tributyltin-2-sulfolene; isomer mixtures of 2-tributyltin-3,4-dimethyl-3-sulfolene, and 2-tributyltin-3,4-dimethyl-2-sulfolene; 2-tributyltin-3-ethyl-4-phenyl-3-sulfolene and 2-tributyltin-3-ethyl-4-phenyl-2-sulfolene; 2-tributyltin-3-naphthyl-4-decyl-3-sulfolene and 2-tributyltin-3-naphthyl-4-decyl-2-sulfolene, and; 2-tributyltin-3,4-dioctyl-2-sulfolene and 2-tributyltin-3,4-dioctyl-3-sulfolene.

In the above procedure the tributyltin chloride is replaced by an equivalent amount of tributyltin bromide, trioctyltin fluoride, trinaphthyltin iodide, tri-p-tolyltin fluoride, and tri-p-methoxyphenyltin iodide, respectively, and the corresponding trialkyltin- and triaryltin-substituted sulfolene isomers are secured.

In the above procedure, the ammonia is replaced by an equivalent amount of methylamine, butylamine, octylamine, phenylamine, dioctylamine and diphenylamine, respectively, and the reaction is carried out at temperatures of 40 C, 75° and 125° C, respectively, and equivalent results are secured.

EXAMPLE IV

Reaction of Sulfolane with
(N,N-dimethylamino)tributyltin

Using the apparatus of Example I, above, 3.6 g. of sulfolane and 10.2 g. of (N,N-dimethylamino)tributyltin were admixed and heated at 150° C for 72 hrs. The reaction product was distilled through a short-path, semi-micro still and the distillate recovered at 160°–170° C (0.05 mm.) was purified further by chromatography. Spectral analysis of the pure product indicated that it corresponded to 2-tributyltin sulfolane. The pot residue from the distillation was found to be 2,5-(bis-tributyltin)sulfolane.

In the above procedure, the sulfolane is replaced by an equivalent amount of 3-methylsulfolane and 3-phenylsulfolane, respectively and the compounds 2-tributyltin-3-methylsulfolane and 2-tributyltin-3-phenylsulfolane are secured.

In the above procedure, the (N,N-dimethylamino)-tributyltin is replaced by an equivalent amount of tris(-tributyltin)amine, bis-(tributyltin)amine, tris-(triphenyltin)amine, and (N,N-diethylamino)tributyltin, respectively, and equivalent results are secured.

EXAMPLE V

| Ingredient | Insecticidal Composition % (wt.) |
|---|---|
| 2-tributyltin-3-methyl-2-sulfolene* | 0.5 |
| Acetone | 10.0 |
| Triton X-100** | 0.1 |
| Water | Balance |

*Prepared in Example I, above.
**(Iso-octylphenylpolyethoxyethanol)

The 2-tributyltin-3-methyl-2-sulfolene is dissolved in the acetone and dispersed in the water using the Triton X-100 emulsifier. The composition is sprayed onto adult houseflies, southern army worm larvae, Mexican bean beetle larvae and adult pea aphids as a pressurized spray and the insects are killed.

In the above composition, the 2-tributyltin-3methyl-2-sulfolene is replaced by an equivalent amount of 2-tributyltin-2-sulfolene, 2-trioctyltinsulfolane, 2-triphenyltin-3-methyl-2-sulfolene, 2-tributyltin-3-sulfolene, and a 1:1 mixture of 2-tributyltin-3-methyl-3-sulfolene and 2-tributyltin-3-methyl-2-sulfolene, respectively, and equivalent results are secured.

EXAMPLE VI

| Ingredient | Acaricidal Composition % (wt.) |
|---|---|
| Mixture of 2-tributyltin-3-methyl-2-sulfolene and 2-tributyltin-3-methyl-3-sulfolene* | 1.0 |
| Acetone | 10.0 |
| Sorbitan mono-oleate polyoxyethylene | 0.25 |
| Water | Balance |

*Isomer mixture prepared in Example II, above.

The tributyltin-substituted sulfolene isomer mixture is dissolved in the acetone and dispersed in the water using the sorbitan mono-oleate polyoxyethylene emulsifier. The composition is sprayed onto bean sprouts infested with the strawberry spider mite and substantially all of the mites are killed within a 24 hour period.

In the above composition, the acetone is replaced by an equivalent amount of kerosene, Stoddard solvent, and ethanol, respectively, and equivalent results are secured.

In the above composition, the sorbitan mono-oleate polyoxyethylene is replaced by an equivalent amount of a mixture of $C_8-C_{18}$ fatty alcohol sulfates, sodium salt form, a mixture of alkyl ($C_9-C_{15}$) benzene sulfonates, sodium salt form, sodium-3-dodecylaminopropionate, and trimethyltetradecylammonium chloride emulsifiers, respectively, and equivalent results are secured.

EXAMPLE VII

| Ingredient | Herbicidal Concentrate % (wt.) |
|---|---|
| 1:1 mixture of 2-tributyltin-2-sulfolene and 2-tributyltin-3-sulfolene | 50 |
| Kerosene | 49 |
| Sorbitan mono-oleate polyoxyethylene | 1.0 |

The above concentrate is admixed with water at a ratio of about 1 pound of concentrate per 100 gallons of water and provides an emulsion. The emulsion is applied to a field infested with pigweed, wild mustard, barnyard grass, and hairy crabgrass at a rate of about 50 gel./acre and the growing weeds are substantially controlled. Seeds from the respective weeds treated in this mannder do not germinate.

The above emulsion is applied to fields planted in corn, soybeans and wheat, at a rate of about 100 gallons per acre and both pre-emergent and post-emergent control of pigweed, wild mustard, barnyard grass, and hairy crabgrass are secured. The growing crops are not substantially damaged by this treatment and are coated with a non-toxic residue of tin oxide at harvest.

As can be seen from the foregoing, the organotin-substituted sulfolene and sulfolane compounds herein can be used to advantage in a variety of pesticidal applications. Furthermore, the compounds herein leave non-toxic tin oxide residues on the treated substrates. Because of the wide biocidal activity of the compounds herein, they are also suitable for use as seed protecting agents. That is to say, seeds treated with one or more of the herein disclosed organotin-substituted sulfolene or sulfolane compounds are protected from the phytopathogenic fungi, especially those of the genus Fusarium. Furthermore, the insecticidal and fungicidal activity of the compounds herein make them admirably suitable for use as wood preservatives in that they protect wood from the ravages of such biological agents as dry rot fungi, sap stain fungi, and all manner of insects, especially termites, boring beetles, and the like. Therefore, it is to be recognized that the process for combating pests herein is intended to encompass these seed protection and wood preserving aspects of the present invention.

The following examples are intended to describe the seed protecting and wood preserving uses of the organotin-substituted sulfolene and sulfolane compounds, but are not intended to be limiting thereof.

EXAMPLE VIII

*Pythium sp.* and *Rhizoctonia sp.* organisms are thoroughly mixed with soil prepared from three parts loam and two parts seed. A 1:1 mixture of 2-tributyltin-2-sulfolene and 2-tributyltin-3-sulfolene is applied to pea seeds at the rate of 1⅔ ounces per 100 pounds of seed by immersion in a dispersion of the organotin compounds in 5% acetone/1% Tween 20/94% water. A substantial increase in the percentage of germinating seeds is achieved with the organotin treated seeds compared with untreated seeds planted in the infested soil.

Equivalent seed protection is secured when seeds are treated with 2-tributyltinsulfolane at 1⅔ oz. per 100 pounds of seed.

EXAMPLE IX

A wood preservative paint composition is prepared as follows:

| Ingredient | % (Wt.) |
|---|---|
| 1:1 Mixture of 2-tributyltin-2-sulfolene and 2-tributyltin-3-sulfolene | 10 |
| Titanium dioxide | 50 |
| Linseed oil | 40 |

The paint is applied to Loblolly pine and gives effective protection against the dry rot fungus, *L. trabea*, as well as against termites and boring beetles. The above composition is applied to wood pilings as an anti-fouling paint and prevents the accumulation of mollusks and barnacles thereon.

In the above composition, the mixture of sulfolene compounds is replaced by an equivalent amount of 2-tributyltinsulfolane, 2-triphenyltin-3-sulfolene, 2-tri-α-chloronaphthyltin-2-sulfolene, 2-tricyclohexyltin-3-sulfolene, 2-tributyltin-3-phenyl-3-sulfolene, 2-trimethyltin-3-α-nitronaphthyl-2-sulfolene, 2-triphenyltinsulfolane, 2-tri-p-propoxyphenyltinsulfolane, and 2-triphenanthryltin-3,4-di-p-bromophenyl-2-sulfolene, respectively, with equivalent results.

We claim:

1. A process for controlling undesirable vegetation comprising applying thereto a herbicidally effective amount of an organotin-substituted compound selected from the group consisting of compounds of the formula

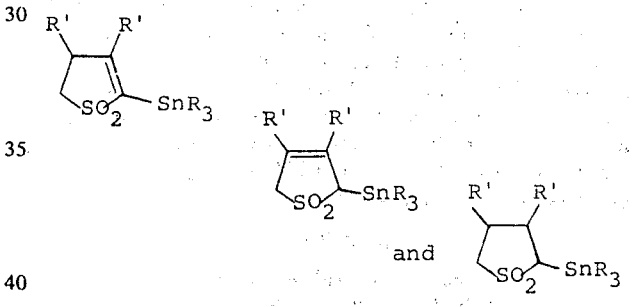

where each R is selected from the group consisting of alkyl of from 1 to about 14 carbon atoms, phenyl, naphthyl, methoxyphenyl, p-chlorophenyl, p-tolyl, m-chlorophenyl, o-fluorophenyl, m-nitrophenyl, α-chloronaphthyl, cyclohexyl, p-propoxyphenyl and phenanthryl, and each R' is selected from the group consisting of alkyl of from 1 to about 14 carbon atoms, phenyl, α-nitronaphthyl, naphthyl, p-tolyl, p-chlorophenyl, o-methoxyphenyl, p-bromophenyl, and hydrogen.

2. A process according to claim 1 wherein the organotin-substituted compound is selected from the group consisting of 2-tributyltin-3-methyl-2-sulfolene, 2-tributyltin-3-methyl-3-sulfolene, 2-tributyltin-2-sulfolene, 2-tributyltin-3-sulfolene, 2-tributyltin-3-methylsulfolane, and 2-tributyltinsulfolane.

* * * * *